United States Patent [19]
Richter et al.

[11] Patent Number: 4,581,434
[45] Date of Patent: Apr. 8, 1986

[54] PROCESS FOR INCREASING THE DURATION OF ACTION OF AGENTS FOR COMBATING PESTS

[75] Inventors: Roland Richter, Cologne; Paul Reinecke, Leverkusen; Hanns P. Müller, Odenthal-Blecher; Edgar Möhring, Bergisch-Gladbach; Wilhelm Brandes, Leichlingen, all of Fed. Rep. of Germany

[73] Assignee: Bayer Aktiengesellschaft, Leverkusen, Fed. Rep. of Germany

[21] Appl. No.: 522,930

[22] Filed: Aug. 12, 1983

[30] Foreign Application Priority Data

Sep. 4, 1982 [DE] Fed. Rep. of Germany ....... 3232916
Oct. 20, 1982 [DE] Fed. Rep. of Germany ....... 3238743

[51] Int. Cl.$^4$ ............................................. C08G 18/38
[52] U.S. Cl. ....................................... 528/49; 528/73; 544/182; 544/321; 548/306
[58] Field of Search .................... 528/49, 73; 544/182, 544/321; 548/306

[56] References Cited

FOREIGN PATENT DOCUMENTS 2901060 7/1980 Fed. Rep. of Germany.
2910356 9/1980 Fed. Rep. of Germany.
2912289 10/1980 Fed. Rep. of Germany.

Primary Examiner—Maurice J. Welsh
Attorney, Agent, or Firm—Sprung Horn Kramer & Woods

[57] ABSTRACT

A process for increasing the duration of action of a pest-combating agent having at least one hydrogen atom which is active in Zerewitinoff reactions but which is not part of a carbamic acid ester group

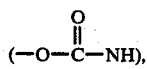

comprising linking the pest-combating agent with a polyether via a difunctional coupling member.

4 Claims, No Drawings

PROCESS FOR INCREASING THE DURATION OF ACTION OF AGENTS FOR COMBATING PESTS

The present invention relates to a new process for increasing the duration of action of agents for combating pests.

Agents having an increased duration of action, that is to say with delayed release of the active compound (slow release properties), are compounds in which a molecule of active compound is chemically bonded to a polymeric carrier and which release the active compound component from the polymeric carrier by hydrolysis or depolymerization under use conditions.

Examples of known processes for the preparation of such compounds are the linking of an active compound containing a reactive group (for example an isocyanate group) with a suitable polymer carrier, such as polyvinyl alcohol (U.S. Pat. No. 4,267,281) or with a polymerizable monomer, such as acrylic acid (U.S. Pat. No. 4,255,693) or with a copolymer containing glycidyl groups (DE-OS [German Published Specification] No. 2,819,340). The disadvantage of these processes is that either the active compound must be chemically modified to obtain functional groups, for example by converting an amine group into an isocyanate group, which is associated with loss of expensive active substance, or derivatives can be formed exclusively only from active compounds containing a hydroxyl group, or, on subsequent polymerization, additional factors besides hydrolysis, such as the rate of depolymerization and the diffusion from the polymer skeleton, influence the release of the active molecule embedded in the polymer, which considerably restricts use because of the poor reproducibility.

It is known that active compounds having a hydrogen atom active in Zerewitinoff reactions can be linked to a polyether containing one OH or NH monofunctional group via a coupling member which has two groups reactive towards hydrogen atoms active in Zerewitinoff reactions; compare DE-OS [German Published Specification] No. 2,901,060, DE-OS [German Published Specification] No. 2,910,356 and DE-OS [German Published Specification] No. 2,912,289. This process is said to improve the solubility of biologically active compounds in water and lower aliphatic alcohols.

It has now been found that the duration of action of pest-combating agents having at least one hydrogen atom which is active in Zerewitinoff reactions but may not be part of a carbamic acid ester group

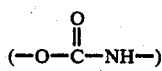

can be increased by linking the pest-combating agent with a polyether via a difunctional coupling member.

The term hydrogen atom active in Zerewitinoff reactions is understood as meaning a hydrogen atom which is bonded, in an organic compound, to a centre which exerts a highly electron-withdrawing action in comparison with a C atom of a hydrocarbon. In the narrower sense, active Zerewitinoff reactions means an H atom which is active in the sense of the reaction: $CH_3MgI + H-X \rightarrow CH_4 + IMgx$ (see also Beyer Lehrbuch der organischen Chemie [Bayer Textbook of Organic Chemistry] (1968) page 147).

The term pest-combating agents is understood as meaning insecticides, acaricides, nematicides, fungicides, bactericides, microbicides, virucides, alficides, herbicides, plant growth regulators and compounds which influence the growth of individual or all stages in the development of insects or acarides. These agents are used in the areas of country and agriculture and in the domestic, hygiene and animal breeding sector.

The compounds formed in this process are known from DE-OS [German Published Specification] Nos. 2,901,060, 2,910,356 and 2,912,289.

Nothing is known of an increase in the duration of action of plant protection agents by this forming of derivatives.

The following pest-combating agents which are used as starting substances may be mentioned as preferred:

(a) active compounds containing one or more aminic groups having at least one free NH radical, it being possible for the NH radical to be part of a heterocyclic radical, (b) active compounds containing one or more hydrazine groups having at least one free NH radical, it being possible for the hydrazine group to be part of a heterocyclic radical, (c) active compounds containing one or more guanidine groups having at least one free NH radical, it being possible for the guanidine group to be part of a heterocyclic radical, (d) active compounds containing one or more alcoholic hydroxyl or mercapto groups, (e) active compounds containing one or more phenolic hydroxyl or mercapto groups, (f) active compounds containing one or more carboxylic acid amide groups having at least one free NH radical, it being possible for the carboxylic acid amide group to be part of a heterocyclic radical, and (g) active compounds containing one or more urea groups having at least one free NH radical, it being possible for the urea group to be part of a heterocyclic radical.

Specific compounds which may be mentioned are:

From group (a): active compounds which contain a free primary or secondary amino group, such as methyl N-(N'-6-aminophenylthiocarbamoyl)-carbamate, heterocyclic compounds with free amino groups, such as 2-aminopyridines, 2-amino-1,3,4-thiadiazoles, 5-amino-4-chloro- or bromo-2-phenyl-pyridazin-3-ones or 4-chloro-5-methylamino-2-(4-trifluoromethylphenyl)-pyridazin-3-one; and furthermore active compounds which contain an aminic NH group as part of a heterocyclic radical, such as, for example, 2-(2-furyl)-benzimidazole.

From group (b): active compounds from the 4-amino-1,2,4-triazine series, such as, for example, 4-amino-6-tert.-butyl-3-(methylthio)-1,2,4-triazin-5(4H)-one and 4-amino-3-methyl-6-phenyl-1,2,4-triazin-5(4H)-one, or maleic acid hydrazide and 3-methyl-4-(2-chlorophenylhydrazono)-1,2-oxazol-5-one, and O,O-diethyl O-(3-methyl-5-pyrazolyl)-thionophosphate.

From group (c): active compounds such as, for example, 3-amino-1,2,4-triazole, 2-chloro-4-ethylamino-6-isopropylamino-1,3,5-triazine, 2-chloro-4-ethylamino-6-(1-cyanoisopropylamino)-1,3,5-triazine, 6-(2-chloroanilino)-2,4-dichloro-1,3,5-triazine and methyl 2-benzimidazolecarbamate and methyl 4- or 5-methylbenzimidazolecarbamate.

From group (d): active compounds from the diphenyl carbinol series, such as, for example, 1,1-bis-(4-chlorophenyl)-2,2,2-trichloroethanol and isopropyl 2,2-bis-(4-chlorophenyl)-2-hydroxyacetate, phosphonic acid esters containing hydroxyl groups, such as, for example, O,O-dimethyl (1-hydroxy-2,2,2-trichloroethyl)-phosphonate, or 3,3-dimethyl-2-hydroxy-1-(4'-phenylphenoxy)-1-(1,2,4-triazol-1-yl)-butane or 9-(carbomethoxy)-2-chloro-9-hydroxyfluorene and 4-hydroxy-3-(1,2,3,4-tetrahydronaphth-1-yl)-2H-chomenone.

From group (e): active compounds such as, for example, 6-tert.-butyl-2,4-dinitrophenol, or heteroaromatics which carry hydroxyl groups, such as, for example, 3-hydroxy-5-methyl-1,2-oxazole, 5-butyl-2-(dimethylamino)-4-hydroxy-6-methylpyrimidine or 5-butyl-2-(ethylamino)-4-hydroxy-6-methylpyrimidine.

From group (f): active compounds from the phosphoric acid ester series, such as, for example, O,O-dimethyl S-(methylaminocarbonylmethylene)-dithiophosphate and O,O-dimethyl S-(methylaminocarbonylmethylene)-thiophosphate, or the phosphoric acid amide O,S-dimethylthionophosphoramide, and heterocyclic compounds in which the amide structure is part of the heterocyclic radical, such as 2-thiono-4-oxo-1,3-thiazolidine.

From group (g): active compounds from the 3-aryl-1,1-dimethylurea series, such as, for example, 4-(3,4-dichlorophenyl)-1,1-dimethylurea, or ureas which contain a heterocyclic radical as a substituent, such as, for example, 1-isobutylaminocarbonyl-2-imidazolinedione, 1,3-dimethyl-5-tert.-butyl-1,3,4-thiadiazol-2-yl)-urea, 1,3-dimethyl-1-(5-trifluoromethyl-1,3,4-thiadiazol-2-yl)-urea and 1-benzo-1,3-thiazol-2-yl)-1,3-dimethylurea, and furthermore active compounds in which the urea structure is entirely present as part of the heterocyclic radical, such as, for example, 4-trichloromethylmercapto-3,5-dioxo-1,2,4-triazolidine, 3-(2-butyl)-5-bromo-6-methyluracil or 3-cyclohexyl-5,6-trimethyleneuracil, and acylureas of the general formula (I)

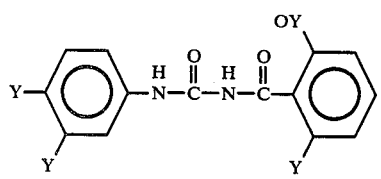

(I)

wherein the radicals Y independently of one another represent hydrogen, halogen or halogenoalkyl or halogenoalkoxy with 1–4C atoms.

Particular examples which may be mentioned are: herbicides, such as, for example, 4-amino-6-tert.-butyl-3-(methylthio)-1,2,4-triazin-5(4H)-one, 4-amino-3-methyl-6-phenyl-1,2,4-triazin-5(4H)-one, 3-(3,4-dichlorophenyl)-1,1-dimethylurea, 1-(benzo-1,3-thiazol-2-yl)-1,3-dimethyl-urea and 1,3-dimethyl-1-(5-ethylsulphonyl-1,3,4-thiadiazol-2-yl)-urea; insecticides, such as, for example, O,O-dimethyl (1-hydroxy-2,2,2-trichloroethyl)-phosphonate and O,S-dimethylthionophosphoramide, and fungicides, such as, for example, 2-(2-furyl)-benzimidazole, 6-(2-chloroanilino)-2,4-dichloro-1,3,5-triazine, 3,3-dimethyl-2-hydroxy-1-(4'-phenylphenoxy)-1-(1,2,4-triazol-1-yl)-butane and methyl 2-benzimidazolecarbamate.

The fungicidal active compounds from the alkyl 2-benzimidazolecarbamate series of the general formula (II)

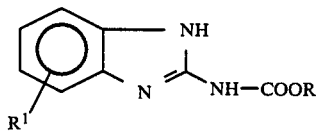

(II)

wherein
R represents alkyl with 1–4C atoms and
R¹ represents alkyl with 1–6C atoms or hydrogen, may be singled out in particular.

Difunctional coupling members which may be mentioned as suitable for the process according to the invention are organic compounds having at least two groups reactive towards hydrogen atoms active in Zerewitinoff reactions.

In this context, preferred compounds which may be mentioned are those of the general formula (III)

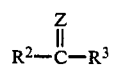

(III)

in which
R² and R³ independently of one another represent halogen, alkyl with 1 to 6C atoms, halogenoalkoxy, alkoxy, alkylmercapto, halogenoalkylmercapto or aryloxy, or
R² and R³, together with the adjacent C atom, represent alkylenedioxy, and
Z represents —O—, —S— or >N—R⁴, wherein
R⁴ represents linear or branched alkyl with 1 to 18C atoms or phenyl or naphthyl which is optionally monosubstituted or polysubstituted by halogen, alkyl, alkoxy, alkylmercapto, halogenoalkyl, halogenoalkylmercapto or phenoxy. Preferably, R² and/or R³ represent halogen and/or alkoxy, in particular methoxy, or phenoxy or ethylenedioxy, and Z represents —O—, —S— or

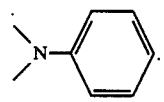

Very particularly preferred compounds of the formula (III) are those in which
R² and R³ represent halogen or alkoxy and
Z represents —O— or —S—.
Compounds of the general formula (IV)

     (IV)

in which R⁵ represents substituted or unsubstituted divalent aliphatic, cycloaliphatic, araliphatic or aromatic hydrocarbon radicals, may also be mentioned as preferred compounds having at least two groups reactive towards hydrogen atoms active in Zerewitinoff reactions.

Preferably, in this formula, R⁵ represents divalent aliphatic hydrocarbon radicals with 2–40C atoms, in particular with 2–18C atoms, which are optionally substituted by halogen, cyano, nitro, optionally substituted alkyl- or aryl-mercapto, alkoxycarbonyl, alkoxysulphonyl, alkoxyphosphoryl, halogenocarbonyl, amidoyl, alkoxy, aryloxy, aryloxycarbonyl, aryloxysulphonyl or aryloxyphosphoryl, aryl representing phenyl or naphthyl which is optionally substituted by C₁–C₆-alkyl, halogen, cyano, nitro, optionally substituted alkoxy, alkylmercapto, aryloxy, arylmercapto or halogenoalkyl.

$R^5$ furthermore preferably represents cycloaliphatic hydrocarbon radicals with 4–15C atoms or aromatic hydrocarbon radicals with 6–15C atoms which are in each case optionally monosubstituted or polysubstituted by alkyl with 1 to 20C atoms, which is optionally monosubstituted or polysubstituted by halogen, cyano, nitro, optionally substituted alkylmercapto, aryl (aryl denoting phenyl or naphthyl which is optionally monosubstituted or polysubstituted by alkyl with 1–6C atoms, halogen, cyano, optionally substituted alkoxy, alkylmercapto, arylmercapto or halogenoalkyl), alkoxycarbonyl, alkoxysulphonyl, alkoxyphosphoryl, halogenocarbonyl, amidoyl, alkoxy, aryloxy, arylmercapto, aryloxycarbonyl, aryloxysulphonyl or aryloxyphosphoryl, aryl in each case having the abovementioned meaning, or by cycloalkyl with 5–20C atoms, which is optionally monosubstituted or polysubstituted by alkyl with 1–6C atoms halogen, cyano, nitro, optionally substituted alkylmercapto, alkoxycarbonyl, alkoxysulphonyl, alkoxyphosphoryl, halogenocarbonyl, amidoyl, alkoxy, aryl, aryloxy, arylmercapto, aryloxycarbonyl, aryloxysulphonyl or aryloxyphosphoryl, aryl in each case having the abovementioned meaning, or by phenyl or naphthyl, which is optionally monosubstituted or polysubstituted by alkyl, halogen, CN, optionally substituted alkoxy, alkylmercapto, alkoxycarbonyl, amidoyl, aryloxy, arylmercapto, aryloxycarbonyl, aryloxysulphonyl or aryloxyphosphoryl, aryl having the abovementioned meaning, or by halogen, cyano, nitro, alkoxycarbonyl, alkoxysulphonyl, alkoxyphosphoryl, halogenocarbonyl, amidoyl, optionally substituted alkoxy, alkylmercapto, aryloxy, aryloxycarbonyl, aryloxysulphonyl or aryloxyphosphoryl, aryl in each case having the abovementioned meaning. $R^5$ furthermore preferably represents araliphatic hydrocarbon radicals with 7–15C atoms, one of the radicals X being bonded to the aliphatic part and the other radical X being bonded to the aromatic part, or both radicals X being bonded to the aliphatic part. Both the aliphatic and the aromatic part can be substituted by the substituents mentioned above in the case of the aromatic hydrocarbons.

X represents identical or different functional groups reactive towards hydrogen atoms active in Zerewitinoff reactions, such as, for example, halogenocarbonyl, alkoxycarbonyl, carboxyl, carboxylic acid anhydride, sulphonic acid, phosphoric acid, isothiocyanate or isocyanate.

$R^5$ particularly preferably represents divalent aliphatic hydrocarbon radicals with 2–18C atoms, which are optionally substituted by halogen, cyano, nitro, alkoxycarbonyl, alkoxysulphonyl, alkoxyphosphoryl, alkoxy, aryloxy, aryloxycarbonyl, aryloxysulphonyl or aryloxyphosphoryl, aryl having the abovementioned meaning.

$R^5$ furthermore particularly preferably represents divalent cycloaliphatic hydrocarbon radicals with 5–10C atoms or aromatic hydrocarbon radicals with 6–13C atoms, which are in each case optionally monosubstituted or polysubstituted by alkyl with 1–4C atoms, which is optionally substituted as described above, and/or by halogen, cyano, nitro, alkoxycarbonyl, alkoxysulphonyl, alkoxyphosphoryl, alkoxy, aryloxy, aryloxycarbonyl, aryloxysulphonyl or aryloxyphosphoryl, aryl having the abovementioned meaning.

$R^5$ furthermore particularly preferably represents divalent aliphatic radicals with 8–13C atoms, which are in each case optionally monosubstituted or polysubstituted by halogen, cyano, nitro, alkoxycarbonyl, alkoxysulphonyl, alkoxyphosphoryl, optionally substituted alkoxy, alkylmercapto, aryloxy, arylmercapto, aryloxycarbonyl, aryloxysulphonyl or aryloxyphosphoryl, aryl having the abovementioned meaning. In addition to the substituents mentioned, the aromatic part of the aliphatic radical may be substituted by $C_{1-4}$-alkyl or halogenoalkyl.

X particularly preferably represents halogenocarbonyl, alkoxycarbonyl, carboxyl, carboxylic acid anhydride or isocyanate.

Very particularly preferred compounds of the general formula (IV) are those in which $R^5$ represents a divalent aliphatic hydrocarbon radical with 2–8C atoms, which is optionally monosubstituted or polysubstituted by $C_{1-4}$-alkoxycarbonyl, and X represents isocyanate.

Particularly suitable compounds are phosgene, thiophosgene, alkyl chloroformates, glycol carbonate, diphenyl carbonate, succinic acid, adipic acid, suberic acid, azelaic acid, sebacic acid, phthalic acid, isophthalic acid, trimellitic acid, tetrahydrophthalic anhydride, endomethylenetetrahydrophthalic anhydride, glutaric anhydride, maleic anhydride, fumaric acid and oleic acid, and ethylene diisocyanate, dodecane-1,12-diisocyanate, cyclobutane-1,3-diisocyanate, cyclohexane-1,4-diisocyanate, 1-isocyanato-3,3,5-trimethyl-5-isocyanatomethylcyclohexane (DE-Auslegeschrift [German Published Specification] No. 1,202,785 and U.S. Pat. No. 3,401,190), hexahydrotoluylene 2,4- and 2,6-diisocyanate, hexahydrophenylene 1,3- and/or 1,4-diisocyanate, perhydrodiphenylmethane 2,4'- and/or 4,4'-diisocyanate, phenylene 1,3- and 1,4-diisocyanate, toluylene 2,4- and 2,6-diisocyanate, diphenylmethane 2,4'- and 4,4'-diisocyanate and naphthylene 1,5-diisocyanate. Very particularly preferred compounds are hexamethylene diisocyanate, toluylene 2,4-diisocyanate, diphenylmethane 4,4'-diisocyanate, isophorone diisocyanate and methyl 1,6-diisocyanato-hexanoate (lysine methyl ester diisocyanate).

Polyethers which may be mentioned as suitable for the process according to the invention are polyethers having one OH, NH or $NH_2$ functional group and at least two to at most four hundred ethylene oxide, propylene oxide or mixed ethylene oxide/propylene oxide block units.

Polyethers of the general formula (V)

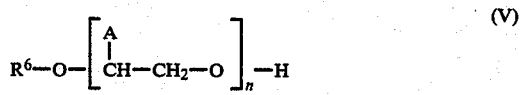

in which
$R^6$ represents an alkyl radical with 1–6C atoms,
A represents hydrogen or methyl and
n represents an integer between 1 and 399, are preferably used.

The preparation of the polyethers is known.

The process according to the invention can be carried out by three different variants:

Process variant (a):

The monofunctional polyether and the difunctional coupling member are reacted in a ratio of 1:1 and the active compound is added onto this monofunctional polyether prepolymer.

Process variant (b):

The difunctional coupling member and the active compound are reacted in a ratio of 1:1 and the monofunctional polyether is added onto this monofunctional active compound derivative.

Process variant (c):

The monofunctional polyether, the difunctional coupling member and the active compound are reacted in a ratio of 1:1:1 in a "one-pot reaction".

The possible process variants are carried out with the various difunctional coupling members as described in DE-OS [German Published Specifications] Nos. 2,901,060, 2,910,356 and 2,919,289.

If the process according to the invention is carried out by variant (a) and a diisocyanate is used as the coupling member, the procedure followed is advantageously as described below.

If, for example, an ethylene oxide polyether started from n-butanol and having a terminal OH group, and hexamethylene diisocyanate and, as the active compound, methyl 2-benzimidazolecarbamate are used, the process according to the invention is to be carried out as follows:

The amount of ethylene oxide polyether corresponding to one equivalent of OH groups is dehydrated in a vacuum of 10 to 200 mm Hg at a temperature of 60°–160° C., preferably 80°–120° C., for 10 minutes to 2 hours, preferably 20 minutes to 60 minutes, and the pressure is then brought to the normal pressure with an inert gas. 0.01 to 1% by weight, based on the amount of ethylene oxide polyether which remains, of an organic carboxylic acid halide, preferably benzyl chloride, is added and the mixture is subsequently stirred at 60°–160° C., preferably 70°–120° C., for 1 to 30 minutes, preferably 5–10 minutes. The amount of OH equivalents, which remain is determined titrimetrically on a sample. An amount of hexamethylene diisocyanate equivalent to the amount of OH which remains is then added, so that an equivalent ratio of OH:NCO of 1:2 is maintained. The mixture is subsequently stirred at a temperature of 60°–160° C., preferably 80°–100° C., care being taken that no moisture enters the apparatus until the calculated residual content of isocyanate has been achieved. The mixture is cooled to give a polyether isocyanate of the ideal formula (VI)

$$H_9C_4O-[(CH_2)_2O]_{\overline{n}}-(CH_2)_{\overline{2}}-O-\overset{O}{\underset{\|}{C}}-NH-(CH_2)_{\overline{6}}-NCO \quad (VI)$$

in which n has the abovementioned meaning.

In a second stage of the process, which immediately follows the first stage, this polyether isocyanate is reacted with one equivalent of active compound at a temperature of 25°–150° C., preferably 70°–140° C., with exclusion of moisture, it being possible for the active compound to be dissolved in an inert solvent. The reaction has proceeded to completion when no further isocyanate can be detected in the reaction mixture by IR spectroscopy. The modified active compound has the general ideal formula (VII):

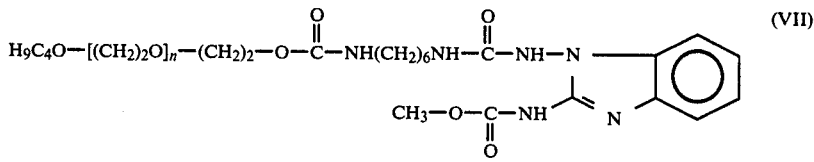

in which n has the abovementioned meaning.

Reactions of other polyethers with a hydroxyl end group with other diisocyanates or polyisocyanates or diisothiocyanates or polyisocyanates and other active compounds according to the invention can, of course, also be carried out in an analogous manner.

In carrrying out variant (b) using a diisocyanate as the coupling member, the procedure followed is advantageously as described below.

The amount of ethylene oxide polyether corresponding to one equivalent of OH groups is dehydrated in a vacuum of 10 to 200 mm Hg at a temperature of 60°–160° C., preferably 80°–120° C., for 10 minutes to 2 hours, preferably 20 minutes to 60 minutes, and the pressure is then brought to the external pressure with an inert gas. 0.01 to 1% by weight, based on the amount of ethylene oxide polyether which remains, of an organic carboxylic acid halide, preferably benzoyl chloride, is added, and the mixture is subsequently stirred at 60°–160° C., preferably 70°–120° C., for 1 to 30 minutes, preferably 5–10 minutes. The amount of OH equivalents which remains is determined titrimetrically on a sample. An amount of hexamethylene diisocyanate such that, based on the OH equivalents of the polyether which remain, an equivalent ratio of OH:NCO of 1:2 is maintained, is then introduced into a second reaction vessel. An amount of active compound, if necessary dissolved in a suitable solvent, such that an equivalent ratio of NCO groups:amino groups of 2:1 is maintained is dissolved in the diisocyanate, with vigorous stirring. The mixture is subsequently stirred at 48°–160° C., preferably 60°–120° C., for 10 minutes to 48 hours and the entire amount of dehydrated polyether is then added. The reaction has proceeded to completion when no further isocyanate can be detected in the reaction mixture by IR spectroscopy.

In this connection, it should be pointed out that the products obtainable both by process variant (a) and by process variant (b) have the same ideal formula only in the case of the compounds X—R⁵—X which are built up symmetrically. In contrast, if a compound which is not built up symmetrically and in which the end groups X are indeed structurally the same (for example both NCO) but are of different reactivity because of their chemical neighborhood, is chosen as the compound X—R⁵—X, the product in which the more reactive end group X has reacted with the first compound used having a hydrogen atom active in Zerewitinoff reactions is always preferentially obtained.

Thus, for example, if an ethylene oxide polyether started from n-butanol, and isophorone diisocyanate and 3-methyl-4-amino-6-phenyl-1,2,4-triazin-5(4H)-one are used, a product of the ideal formula (VIII)

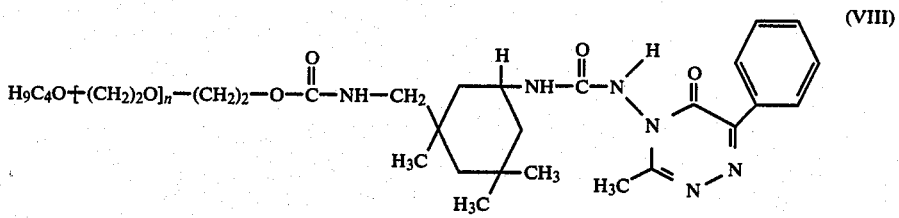

in which n has the abovementioned meaning, is obtained by process variant (a), while a product of the ideal formula (IX)

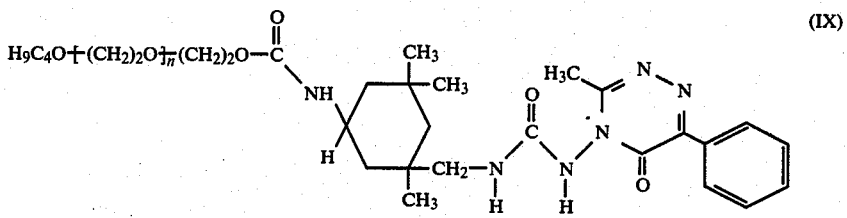

in which n has the abovementioned meaning, is obtained by process variant (b).

In carrying out process variant (c) according to the invention, the procedure followed is advantageously as described below.

If, for example, an ethylene oxide/propylene oxide block copolyether started from n-butanol and having a terminal hydroxyethylene group, and methyl 1,6-diisocyanatohexanoate and N'-(4-chlorophenyl)-N-(2,6-difluorobenzoyl)-urea are used, the process according to the invention is to be carried out as follows:

The amount of polyether corresponding to one equivalent of OH groups is dehydrated under a vacuum of 10 to 200 mm Hg at a temperature of 60°-160° C., preferably 80°-120° C., for 5 minutes to 1 hour, preferably 10 minutes to 30 minutes, and the pressure is then brought to the external pressure with an inert gas. 0.01 to 1% by weight, based on the amount of polyether which remains, of an organic carboxylic acid halide, preferably benzoyl chloride, is then added and the mixture is subsequently stirred at 60°-160° C., preferably 70°-120° C., for 1 to 30 minutes, preferably 5-10 minutes. The amount of OH equivalents which remain is determined titrimetrically on a sample. The required amount of active compound, if necessary dissolved in a suitable solvent, is then added in a ratio of OH equivalents of the polyether:aromatically substituted NH of the active compound of 1:1. The mixture is homogenized, and the required amount of diisocyanate in the equivalent ratio of sum (OH equivalents of the polyether + aromatically substituted NH equivalents of the active compound): sum of all the NCO equivalents of 1:1 is then added dropwise. The mixture is subsequently stirred at 60°-120° C. for 10 minutes to 48 hours, with exclusion of moisture. Where relevant, the solvent is then stripped off in vacuo. The modified active compound has the ideal formula (X):

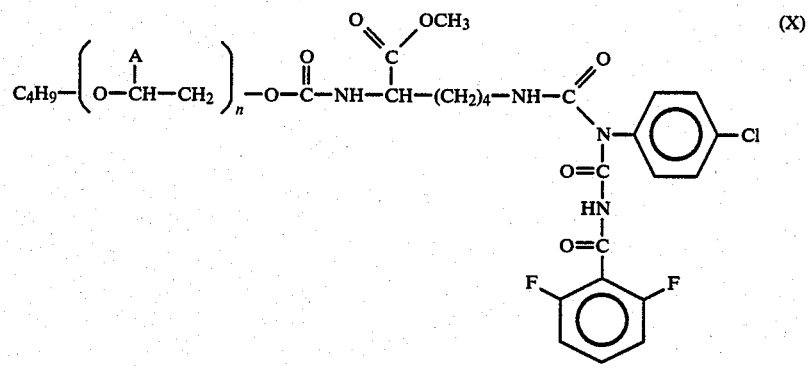

in which A and n have the abovementioned meaning.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in their commercially available formulations and in the use forms prepared from these formulations as mixtures with other active compounds, such as insecticides, attractants, sterilising agents, acaricides, nematicides, fungicides, growth-regulating substances or herbicides. Examples of insecticides include phosphoric acid esters, carbamates, carboxylic acid esters, chlorinated hydrocarbons, phenylureas, substances produced by microorganisms and the like.

The active compounds according to the invention can furthermore be present in their commercially available formulations and in the use forms prepared from these formulations as mixtures with synergistic agents. Synergistic agents are compounds which increase the action of the active compounds, without the synergistic agent added having itself to have an effective action.

The active compound content of the use forms prepared from the commercially available formulations can vary within wide limits. The active compound concentration in the use forms can be from 0.0000001 up to 95% by weight of active compound, preferably between 0.0001 and 1% by weight.

The active compounds are used in the customary manner suited to the use forms.

EXAMPLE 1

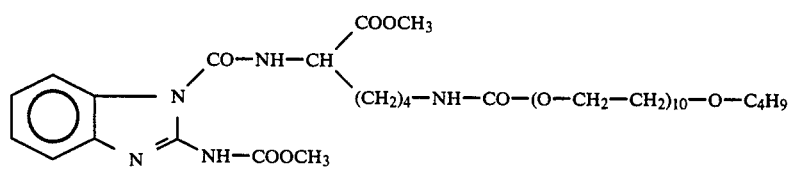

78.0 g (0.15 mol) of a monofunctional ethylene oxide polyether which has been started from n-butanol, has an average molecular weight of 520 (average number of ethylene oxide units n=10) and has been dehydrated beforehand at 120° C. under 20 mbar for 30 minutes, are stirred with 1 ml of benzoyl chloride and 31.8 g (0.15 mol) of lysine methyl ester diisocyanate at 90° C. under a dry nitrogen atmosphere. After 35 minutes, the NCO content has dropped to the calculated value of 5.7% by weight. 28.7 g (0.15 mol) of methyl 2-benzimidazolyl-carbamate (MBC) and 350 ml of absolute toluene are now added to this solution and stirring is continued at 100° to 110° C. until the isocyanate band at 2260 cm$^{-1}$ in the IR spectrum has completely disappeared. The toluene is then stripped off again in vacuo. 138 g of a waxy paste having a softening point of 45°–50° C. (clear melt) are obtained; active compound content=20.7%.

It can also be seen that the linkage is complete by the fact that the new modified active compound is soluble in chloroform or methanol to give a clear solution; MBC has only a poor solubility in these solvents.

EXAMPLE 2

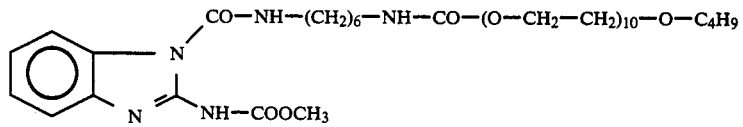

131 g of a pasty composition having a softening point of 48°–52° C. (clear melt) and an active compound content of 21.8% are obtained analogously to Example 1, but with 25.2 g of hexamethylene diisocyanate.

EXAMPLE 3

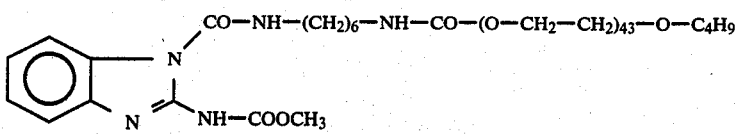

1,180 g of a solid with a softening point of 80°–85° C. and an active compound content of 8.1% are obtained from 1,000 g (0.5 mol) of an ethylene oxide polyether started from n-butanol and having an average molecular weight of 2,000, 84 g (0.5 mol) of hexamethylene diisocyanate and 95.5 g (0.5 mol) of MBC analogously to Example 1.

EXAMPLE 4

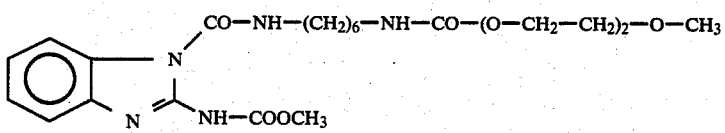

479 g of a solid with a melting point of 137° C. and an active compound content of 40% are obtained from 120 g (1 mol) of diethylene glycol monomethyl ether, 168 g (1 mol) of hexamethylene diisocyanate and 191 g of methyl 2-benzimidazolylcarbamate analogously to Example 1.

EXAMPLE 5

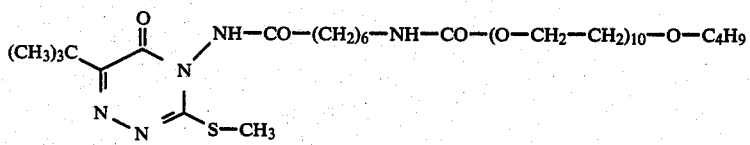

135 g of a yellowish viscous product with an active compound content of 23.7% are obtained analogously to Example 1, but using 25.2 g of hexamethylene diisocyanate and 32.1 g of 4-amino-6-tert.-butyl-3-(methylthio)-1,2,4-triazin-5(4H)-one. Analytical detection of the linkage is carried out by $^1$H NMR spectroscopy [disappearance of the amino protons (5.9 ppm) and new NH band at a lower field (9.00 ppm)] and by quantitative liquid chromatography (internal standard: diphenyl ketone), and shows that only 1.9 g of the active compound (=6.7%) is still present in non-bonded form.

EXAMPLE 6

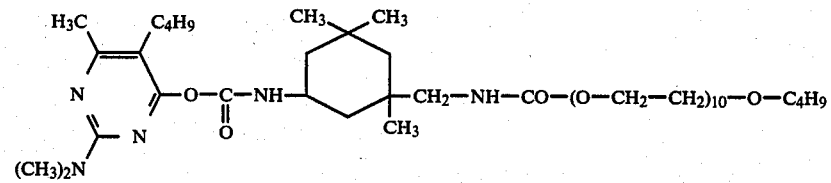

140 g of a pasty solid which has a softening point of 45°–50° C., giving a clear melt, and an active compound content of 20.6% are obtained analogously to Example 1, but using 33.3 g of isophorone diisocyanate and 29 g of 5-butyl-2-(dimethylamino)-4-hydroxy-6-methylpyrimidine.

EXAMPLE A

Comparison of the rate of hydrolysis

The rate of degradation by hydrolysis was determined in i-propanol/water 1:1 at pH 7 and 40° C. The active compound concentration relates to the actual content of active compound (±2–3 ppm).

TABLE

| Compounds used | Example 1 (according to the invention) | (known) | Example 5 (according to the invention) | (known) |
|---|---|---|---|---|
| Starting concentration | 100 ppm | 100 ppm | 100 ppm | 100 ppm |
| after 15 days | 80 ppm | 70 ppm | 85 ppm | 75 ppm |
| after 30 days | 70 ppm | 60 ppm | 75 ppm | 60 ppm |
| after 45 days | 60 ppm | 50 ppm | 70 ppm | 55 ppm |
| after | 55 ppm | 40 ppm | 65 ppm | 50 ppm |

TABLE-continued

| Compounds used | Example 1 (according to the invention) | 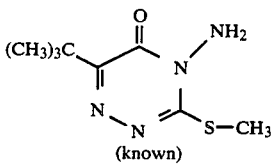(known) | Example 5 (according to the invention) | 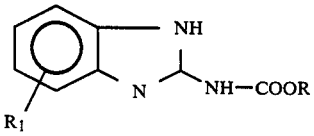(known) |
|---|---|---|---|---|
| 60 days after 90 days | 45 ppm | 25 ppm | 55 ppm | 35 ppm |

EXAMPLE 7

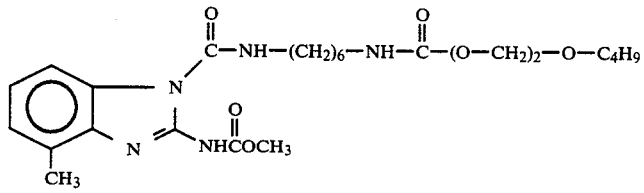

134 g of a solid with a melting point of 118° C. and an active compound content of 38.3% are obtained from 40.5 g (0.25 mol) of diethylene glycol monobutyl ether, 42.0 g (0.25 mol) of hexamethylene diisocyanate and 51.2 g (0.25 mol) of methyl 4-methyl-2-benzimidazolyl-carbamate analogously to Example 1.

EXAMPLE 8

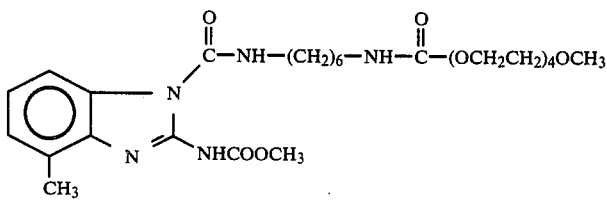

145 g of a solid with a melting point of 92° C. and an active compound content of 35.3% are obtained from 52.0 g (0.25 mol) of tetraethylene glycol monomethyl ether, 42.0 g (0.25 mol) of hexamethylene diisocyanate and 51.2 g (0.25 mol) of methyl 4-methyl-2-benzimidazolylcarbamate analogously to Example 1.

It will be understood that the specification and examples are illustrative but not limitative of the present invention and that other embodiments within the spirit and scope of the invention will suggest themselves to those skilled in the art.

What is claimed is:

1. A process for increasing the duration of action of a pest-combating agent having at least one hydrogen atom which is active in Zerewitinoff reactions but which is not part of a carbamic acid ester group

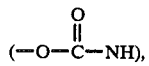

comprising linking a pest-combating agent of the formula wherein $R$ represents alkyl with 1–4C atoms and
$R^1$ represents alkyl with 1–6C atoms, or hydrogen, with a polyether via a difunctional coupling member.

2. A process according to claim 1, wherein the coupling member is of the formula

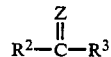

in which
$R^2$ and $R^3$ independently of one another represent halogen, halogenoalkoxy, alkoxy, alkylmercapto, halogenoalkylmercapto or arlyloxy, or
$R^2$ and $R^3$, together with the adjacent C atom of the C=Z form a ring with $R^2$ and $R^3$ representing alkylenedioxy, and
Z represents —O—, —S— or >N—R⁴,
wherein
$R^4$ represents linear or branched alkyl with 1 to 18C atoms or phenyl or naphthyl which is optionally monosubstituted or polysubstituted by halogen, alkyl, alkoxy, alkylmercapto, halogenoalkyl, halogenoalkylmercapto or phenoxy.

3. A process according to claim 1, wherein the coupling member is of the formula

in which
- $R^5$ represents substituted or unsubstituted divalent aliphatic, cycloaliphatic, araliphatic or aromatic hydrocarbon radicals; and
- X represents halogenocarbonyl, alkoxycarbonyl, carboxyl, carboxylic acid anhydride or isocyanate.

4. A process according to claim 1, wherein the polyether is of the formula

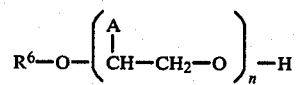

in which
- n represents an integer between 1 and 399;
- $R^6$ represents an alkyl radical with 1 to 6C atom; and
- A represents hydrogen or methyl.

* * * * *

UNITED STATES PATENT AND TRADEMARK OFFICE
CERTIFICATE OF CORRECTION

PATENT NO. : 4,581,434
DATED : April 8, 1986
INVENTOR(S) : Roland Richter, et al.

It is certified that error appears in the above-identified patent and that said Letters Patent is hereby corrected as shown below:

Col. 1, line 21          Delete "4,255,693" and substitute --4,225,693--

Col. 7, line 43          Delete "benzyl" and substitute --benzoyl--

Cols. 13-14, Table, and Cols. 15-16          Heading of 3rd column delete upper right of formula and substitute

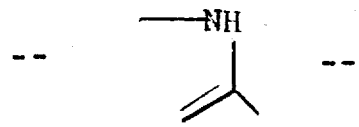

Signed and Sealed this

Fifteenth Day of July 1986

[SEAL]

Attest:

DONALD J. QUIGG

Attesting Officer      Commissioner of Patents and Trademarks